(12) United States Patent
Argenta et al.

(10) Patent No.: US 11,931,166 B2
(45) Date of Patent: Mar. 19, 2024

(54) SYSTEM AND METHOD OF DETERMINING AN ACCURATE ENHANCED LUND AND BROWDER CHART AND TOTAL BODY SURFACE AREA BURN SCORE

(71) Applicant: Applied Research Associates, Inc., Albuquerque, NM (US)

(72) Inventors: Christopher Argenta, Albuquerque, NM (US); Aaron Williams, Albuquerque, NM (US); Greg Foderaro, Albuquerque, NM (US); Thomas Paniagua, Albuquerque, NM (US)

(73) Assignee: Applied Research Associates, Inc., Albuquerque, NM (US)

( * ) Notice: Subject to any disclaimer, the term of this patent is extended or adjusted under 35 U.S.C. 154(b) by 650 days.

(21) Appl. No.: 16/922,598

(22) Filed: Jul. 7, 2020

(65) Prior Publication Data
US 2022/0008001 A1 Jan. 13, 2022

(51) Int. Cl.
*A61B 5/00* (2006.01)
*G06T 7/00* (2017.01)
(Continued)

(52) U.S. Cl.
CPC ............ *A61B 5/445* (2013.01); *A61B 5/0013* (2013.01); *A61B 5/0075* (2013.01); *A61B 5/0077* (2013.01); *A61B 5/6898* (2013.01); *A61B 5/7264* (2013.01); *A61B 5/7282* (2013.01); *A61B 5/743* (2013.01); *A61B 5/744* (2013.01); *G06T 7/0014* (2013.01); *G06T 11/206* (2013.01); *G06T 19/20* (2013.01);
(Continued)

(58) Field of Classification Search
CPC ..... A61B 5/445; A61B 5/0013; A61B 5/0075; A61B 5/0077; A61B 5/6898; A61B 5/7264; A61B 5/7282; A61B 5/743; A61B 5/744; A61B 2576/02; G16H 50/20; G06V 20/20; G06V 10/42; G06V 10/143; G06V 10/44; G06V 2201/03; G06T 7/0014; G06T 11/206; G06T 19/20; G06T 2219/2016; G06T 2207/30196; G06T 11/00; G06T 7/174; G06T 2207/30088; G06T 2207/20212; G06T 15/40
See application file for complete search history.

(56) References Cited

U.S. PATENT DOCUMENTS 9,068,887 B1 * 6/2015 Bennouri ................ G01W 1/02
2022/0142484 A1 * 5/2022 DiMaio .................. G16H 50/20

* cited by examiner

*Primary Examiner* — Vu Le
*Assistant Examiner* — Winta Gebreslassie
(74) *Attorney, Agent, or Firm* — Erise IP, P.A.

(57) ABSTRACT

A system and method of generating an enhanced Lund and Browder chart and total body surface area burn score is described herein. In some embodiments, a plurality of images is obtained from of a patient using a camera system. The images may be taken by aligning the patient's body with pose templates presented on a display of the camera system. The non-skin portions of the images may be removed, and skin analysis performed on the skin portion to determine burn location, coverage, and depth. Further, landmarks may be detected in the images to morph and align the images with the pose templates to obtain standard poses. The plurality of images may be combined and presented in two-dimensional and three-dimensional models with labels and the total surface area burn score.

20 Claims, 8 Drawing Sheets

(51) Int. Cl.
*G06T 11/20* (2006.01)
*G06T 19/20* (2011.01)
*G06V 10/143* (2022.01)
*G06V 10/42* (2022.01)
*G06V 10/44* (2022.01)
*G06V 20/20* (2022.01)
*G16H 50/20* (2018.01)

(52) U.S. Cl.
CPC ............ *G06V 10/143* (2022.01); *G06V 10/42* (2022.01); *G06V 10/44* (2022.01); *G06V 20/20* (2022.01); *G16H 50/20* (2018.01); *A61B 2576/02* (2013.01); *G06T 2219/2016* (2013.01); *G06V 2201/03* (2022.01)

SYSTEM AND METHOD OF DETERMINING AN ACCURATE ENHANCED LUND AND BROWDER CHART AND TOTAL BODY SURFACE AREA BURN SCORE

GOVERNMENT LICENSE RIGHTS

This invention was made with government support under NGA Project Announcement #W81XWH-17-C-0150 awarded by the USA Medical Research Acquisition Activity (USAMRAA). The government has certain rights in the invention.

BACKGROUND

1. Field

Embodiments of the invention relate to developing an enhanced Lund and Browder chart. Specifically, embodiments of the invention relate to detecting burned skin to develop an enhanced Lund and Browder chart for determining an accurate total body surface area burn percentage.

2. Related Art

Typically, when a person is burned and is not in close proximity to a medical facility, on-site inexperienced providers need to determine the severity of burns and tend to the burns. Approximately 10%-15% of combat casualties require rapid, accurate assessment of a patient's Total Body Surface Area (TBSA) burned to determine the severity of the burn and the treatment. Triage, resuscitation, wound care, evacuation, and resource planning are performed based on this initial assessment. Because the inexperienced providers are not burn experts, the estimate of the percent of TBSA burned may be off by as much as 50%-100%. Consequently, suboptimal burn care is provided to the patients.

In a typical medical facility with experienced burn care experts, photographs are often taken of the burn(s) as part of the admission process. Additionally, the on-site providers use a paper or digital standard Lund and Browder (LB) diagram and manually color in burned areas and using standard colors to indicate burn severity. A standard Lund and Browder chart is a diagram of the anterior and posterior view of an idealized human body that medical staff can use to record the location and types of wounds on a burn patient. If the burn patient's body shape and size differs from the ideal shape and size of the standard LB diagram this manual process introduces error into the evaluation. When estimating the percent TBSA burned with a standard Lund and Browder chart, the human body is notionally subdivided into different regions (e.g., arm, leg, torso, and head) and each region is given a standard percent of the entire body. The standard percentage of the surface area of the body that is used in the standard LB chart is referred to as the rule of nines. For example, for an adult, the head and neck accounts for 9% of the body surface area, the trunk (torso) accounts for 18% for the anterior and 18% for the posterior, each leg accounts for 18% and so forth. The LB diagram and percentages vary according to a set of age ranges (e.g., adult or infant), but the process remains generally the same. This process gives the medical staff an objective reference to estimate the percent TBSA burned on the patient more consistently. As described above, the medical staff in the field typically have minimal experience with burns and determining burn severity, and can dramatically overestimate or underestimate the burn surface area and severity. Manually mapping between the actual patient and an idealized patient shape and size in the LB compounds this error.

What is needed is a system and method for accurately and automatically determining a patient-specific body diagram with reference to burn size and locations, depth of the burns, and percent TBSA burned. In some embodiments, photographs of the body of the patient may be taken using any combination of Red Green Blue (RGB) visual images as well as multispectral infrared and depth sensing. The photographs and models may be analyzed using machine learning algorithms to identify and map the wounds to individualized, digital, patient-specific body diagrams referenced herein as an enhanced Lund and Browder chart (eLB). Accurate burn locations, depth of burn, and percent TBSA burned estimates may be determined from the images and modeled with two-dimensional and three-dimensional eLB diagrams.

SUMMARY

Embodiments of the invention solve the above-mentioned problems by providing a system that determines the eLB and computes the % TBSA burned using a plurality of images of the burn patient. A first embodiment of the invention is directed to a method of creating an enhanced Lund and Browder chart and determining a total body surface area burn score for a patient with burns, the method comprising the steps of obtaining, by at least one camera, a plurality of images of the patient with burns, wherein the patient is positioned based on at least one pose template presented to a user via a display associated with the at least one camera, recognizing patient body landmarks in the plurality of images, recognizing patient skin regions in the plurality of images, recognizing a background in the plurality of images, recognizing distractors in the plurality of images, recognizing burn locations on the patient in the plurality of images, combining the plurality of images to create the enhanced Lund and Browder chart, and determining the total body surface area burn score based at least in part on the enhanced Lund and Browder chart.

A second embodiment of the invention is directed to a system for creating an enhanced Lund and Browder chart and determining a total body surface area burn score of a patient with burns comprising at least one camera configured to obtain a plurality of images of a patient, a mobile device comprising at least one processor and a display, wherein the at least one camera is communicatively coupled to the mobile device, and one or more non-transitory computer-readable media storing computer-executable instructions that, when executed by the at least one processor, perform a method of creating the enhanced Lund and Browder chart and determining the total body surface area burn score, the method comprising the steps of displaying a plurality of pose templates on the display of the mobile device, obtaining the plurality of images from the at least one camera, recognizing patient skin regions in the plurality of images, recognizing a background in the plurality of images, recognizing distractors in the plurality of images, recognizing burn locations on the patient in the plurality of images, combining the plurality of images to create the enhanced Lund and Browder chart, and determining the total body surface area burn score based at least in part on the enhanced Lund and Browder chart.

A third embodiment of the invention is directed to a one or more non-transitory computer-readable media storing computer-executable instructions that, when executed by at least one processor, perform a method of creating an enhanced Lund and Browder chart and determining a total body surface area burn score of a patient with burns, the method comprising the steps of displaying a plurality of pose templates on a display of a mobile device, obtaining a plurality of images from at least one camera associated with the mobile device, recognizing patient body landmarks in the plurality of images, recognizing skin of the patient in the plurality of images, recognizing burn locations on the skin of the patient in the plurality of images, combining the plurality of images to create the enhanced Lund and Browder chart, determining the total body surface area burn score, and presenting the Lund and Browder chart and the total body surface area burn score via the mobile device.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 1:
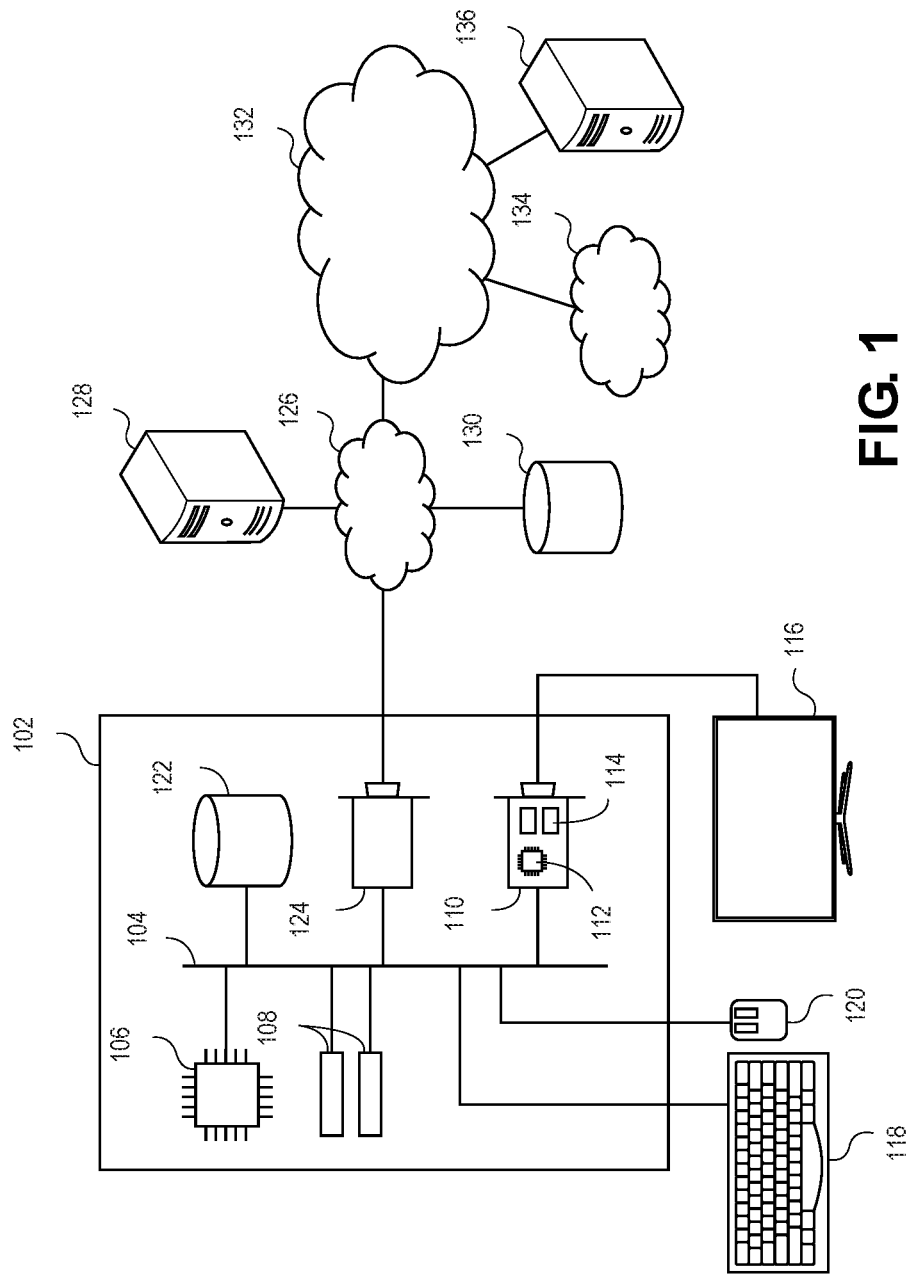
FIG. 1 depicts an exemplary hardware system for implementing embodiments of the invention.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the technology can include a variety of combinations and/or integrations of the embodiments described herein.

Generally, some embodiments of the invention are directed to providing an enhanced Lund and Browder (eLB) chart and determining an accurate Total Body Surface Area (TBSA) burn estimation. Some embodiments utilize images of a burn victim's body to analyze and determine burn location, coverage, and burn depth. The images of the body may be stitched together using software executing embodiments of the invention to create both two-dimensional and three-dimensional models of the patient's body with the burns. The models may be used to determine accurate TBSA burn scores for the patient. Further, the images and burn scores may be shared interactively for evaluation by an expert.

Turning first to FIG. 1, an exemplary hardware platform that can form one element of certain embodiments of the invention is depicted. Computer 102 can be a desktop computer, a laptop computer, a server computer, a mobile device such as a smartphone or tablet, or any other form factor of general- or special-purpose computing device. Depicted with computer 102 are several components, for illustrative purposes. In some embodiments, certain components may be arranged differently or absent. Additional components may also be present. Included in computer 102 is system bus 104, whereby other components of computer 102 can communicate with each other. In certain embodiments, there may be multiple busses or components may communicate with each other directly. Connected to system bus 104 is central processing unit (CPU) 106. Also connected to system bus 104 are one or more random-access memory (RAM) modules 108. Also connected to system bus 104 is graphics card 110. In some embodiments, graphics card 110 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also, on graphics card 110 is GPU memory 114. Connected (directly or indirectly) to graphics card 110 is display 116 for user interaction. In some embodiments no display is present, while in others it is integrated into computer 102. Similarly, peripherals such as keyboard 118, mouse 120, and touchscreen 116 are connected to system bus 104. Like display 116, these peripherals may be integrated into computer 102 or absent. Also connected to system bus 104 is local storage 122, which may be any form of computer-readable media and may be internally installed in computer 102 or externally and removeably attached.

Computer-readable media include both volatile and nonvolatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-useable instructions, data structures, program modules, and other data representations.

Finally, network interface card (NIC) 124 is also attached to system bus 104 and allows computer 102 to communicate over a network such as network 126. NIC 124 can be any form of network interface known in the art, such as Ethernet, ATM, fiber, Bluetooth, or Wi-Fi (i.e., the IEEE 802.11 family of standards). NIC 124 connects computer 102 to local network 126, which may also include one or more other computers, such as computer 128, and network storage, such as data store 130. Generally, a data store such as data store 130 may be any repository from which information can be stored and retrieved as needed. Examples of data stores include relational or object-oriented databases, spreadsheets, file systems, flat files, directory services such as LDAP and Active Directory, or email storage systems. A data store may be accessible via a complex API (such as, for example, Structured Query Language), a simple API providing only read, write and seek operations, or any level of complexity in between. Some data stores may additionally provide management functions for data sets stored therein such as backup or versioning. Data stores can be local to a single computer such as computer 128, accessible on a local network such as local network 126, or remotely accessible over Internet 132. Local network 126 is in turn connected to Internet 132, which connects many networks such as local network 126, remote network 134 or directly attached computers such as computer 136. In some embodiments, computer 102 can itself be directly connected to Internet 132.

In general, images of a burn victim's body may be taken by non-expert persons when the victim is not in close proximity to a medical facility, by clinicians as part of admission to a medical facility, or throughout burn-care to monitor progress. The images may be taken using any combination of Red-Greed-Blue (RGB), Infrared (IR), and depth imagery. The images may be utilized to create the eLB diagram for determining an accurate TBSA burn score and/or recording patient state for health records and monitoring. Embodiments of the invention automatically separate a patient's body from a background in an image or a plurality of images and map the plurality of images into a standard pose but patient-specific anatomical view (the eLB diagram) capable of annotation. The images are also analyzed to determine burn regions on the body such that the burns may be mapped onto the eLB. The burn models may be determined using at least one Neural Network trained using a database of known burn images. Various depth and severity of burns may be determined and assigned to the burn locations in the images. The burn classifications may show superficial, partial thickness, and full thickness burns such that treatment recommendations may be recommended.

Figure 2:
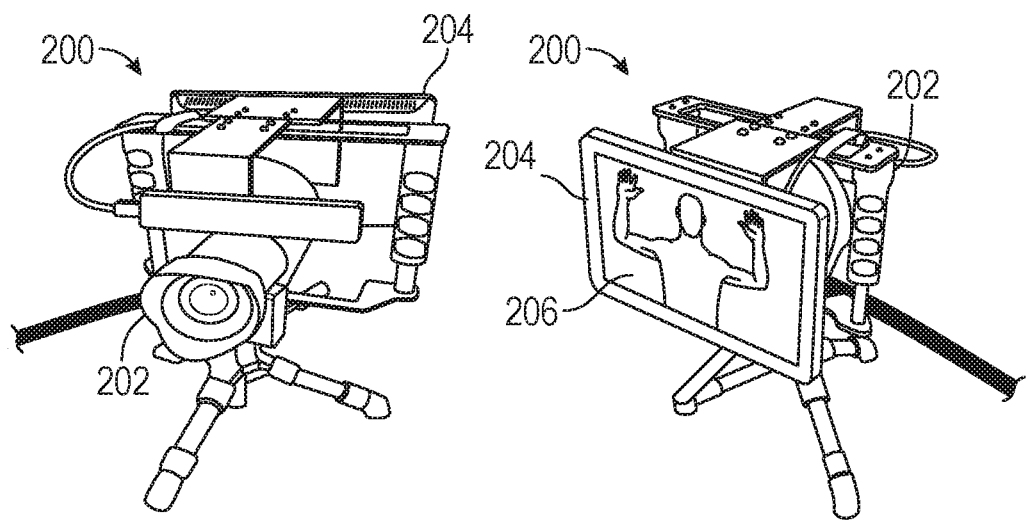
FIG. 2 depicts an exemplary camera system for implementing embodiments of the invention.

FIG. 2 depicts an exemplary camera system 200 that may be used to obtain images of the patient's body for embodiments of the invention and communicatively coupled to a mobile device 204 for processing the images. A camera 202 may be an RGB camera for taking color images. In some embodiments, the camera 202 is an infrared camera and collects light in the infrared spectrum. In some embodiments, the camera 202 may be a Multi-Spectral Image (MSI) camera obtaining multiple images across the spectrums. In some embodiments, the camera may be a thermal imaging sensor to record skin temperature. In some embodiments, the camera 202 is a depth sensor and collects distances from the camera 202. Any combination of the above-described cameras may be used to collect a plurality of images that may be combined to create two-dimensional and three-dimensional models of the patient.

In some embodiments, the camera system 200 may include a mobile device 204 that may be any tablet, phone, laptop, and any other portable computer as described in reference to FIG. 1 above. In some embodiments, the camera system may be attached to a remote computer or any standard medical computing devices.

The camera system 200 may be used outside of medical facilities, at temporary mobile medical facilities in remote locations around the world, or inside medical facilities. Further, the environments where the camera system 200 may be used may be crowded and chaotic with a plurality of injured patients and many inexperienced medical personnel working to help the patients. To work in such an environment, the camera system 200 may be mobile and lightweight with an internal power source (i.e., battery). The camera system 200 may be battery powered such that there are no cords that may be in the way of the healthcare workers. The camera system 200 may be easily operated and easily transported around the patient to obtain images of the patent that may be used to analyze and generate an accurate eLB diagram.

Further, the camera system 200 may be operable to perform the methods described herein automatically with minimal user interaction. In some embodiments, the camera system may comprise biometric recognition software such as, for example, facial recognition, automatic detection of bodies and poses, and voice recognition such that the user may operate the camera system using audible commands.

Figure 3:
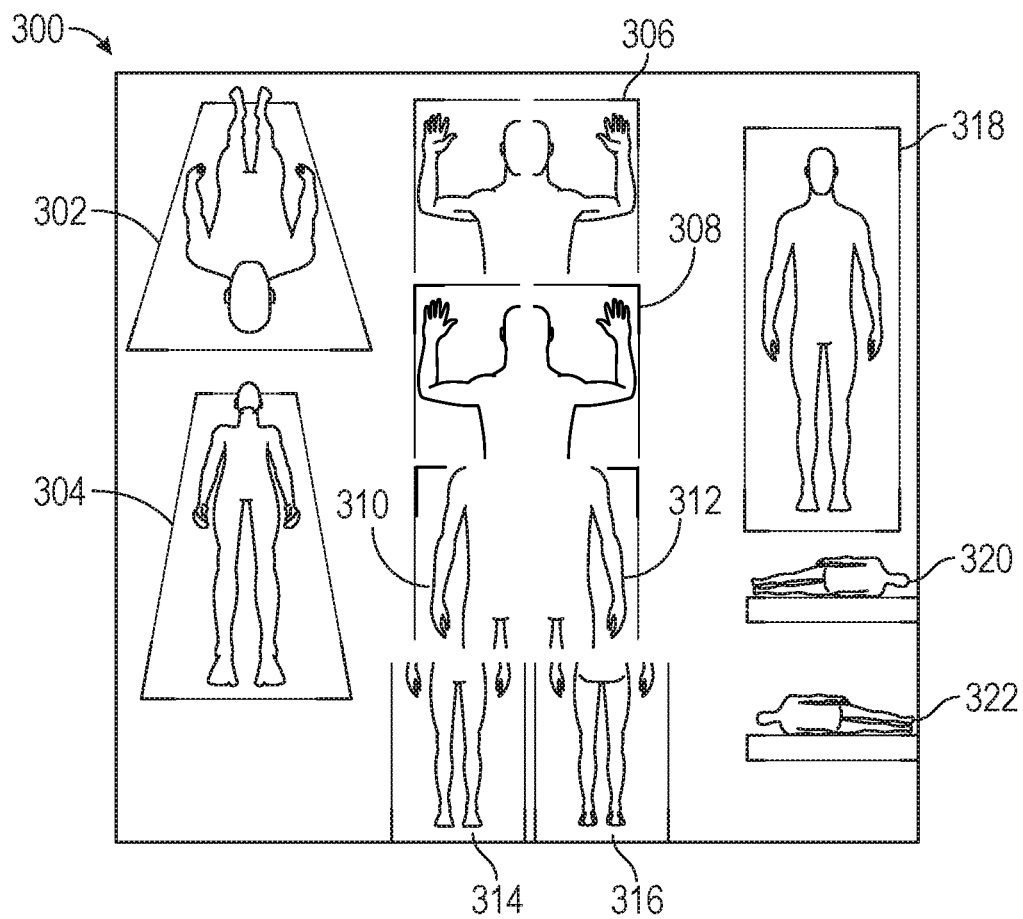
FIG. 3 depicts an embodiment of a plurality of body pose templates.

In some embodiments, a stored database of poses may be presented to the user in a particular order to standardize the method and order of the images captured by the user utilizing the camera system 200. FIG. 3 depicts exemplary pose templates 300. Each pose may be presented on a display screen 206 of the mobile device 204 of the camera system 200 while the user takes the photograph of the patient so that the user may match the patient's body pose to the pose template 300. Presenting the pose templates 300 on the display screen 206 such that the user may match the patient pose to the displayed pose templates 300 ensures that the images captured more closely match the expected pose presented by the pose templates 300. When the patient pose matches the pose templates 300, body landmarks and the edge of the body of the user may be within known regions such that the entire image may not need to be analyzed to find other body landmarks and inform the determination the skin, body, clothes, hair, background, and ultimately, burn location, and burn characteristics.

The pose templates 300 may provide a series of various poses and points of view to which the user must match the patient pose. The user may move around the patient changing the user location and the patient orientation to capture images of the patient matching the displayed templates. The pose templates may be configured to establish a standard process for the set of desired admission photos. In some embodiments, displaying the templates may be customizable and the user may turn off the template displays to view only the presented live image of the patient on the display.

FIG. 3 depicts eleven exemplary poses of the pose templates 300 that were vetted with burn-care experts and determined to be feasible. The user may position the patient and the camera system 200 to capture the first pose 302. The first pose 302 may be an image presented on the display screen 204 of a patient lying flat on their back with their arms at their side. The image may be taken while standing at the head of the bed of a prone patient as shown. The second pose 304 may present the patient in the same position as the first pose 302 but the image is captured from the user at the foot of the bed. The third pose 306 may present the patient either standing or laying down with the patient positioned facing the camera system with both hands raised with the elbows at approximately a 90-degree angle. The fourth pose 308 may present the patient in the same position as in the third pose. However, in the fourth pose 308, the image may be captured from behind the patient. The fifth pose 310 and the sixth pose 312 present the left and right side of the torso of the patient with the arms at the patient's sides. The seventh pose 314 and the eighth pose 316 present the patient's legs from the anterior and the posterior. The ninth pose 318 presents the posterior of the patient in a standing position or directly overhead while laying flat. The tenth pose 320 and the eleventh pose 322 present the anterior and the posterior of the patient with the patient laying on their side. These poses are exemplary. Any pose and order of poses may be used that may capture the body such that the images may be composited and may be analyzed to determine the burn or wound severity.

In some embodiments, capturing all poses is not possible. The patient may be injured such that they cannot stand or may not be able to lay in certain positions for capturing the poses. Alternatively, known unburnt areas can be excluded from capturing. Any number of poses may be used to analyze the patient. Further, the images may be morphed, translated, and modifications may be made to the perspective to align the images with the pose templates when alignment is imperfect. Modifying the images to align with the poses allows machine learning algorithms to accurately analyze the images while providing an eLB unique to the individual patient.

The pose templates 300 provide a method for capturing images of the patient's body such the full surface area can be captured. Using pose templates ensures that the user composes the image in ways that avoid important features from falling outside the captured image frame. Using known poses enforces the expectation that body landmarks are captured in the images and may be determined more accurately and efficiently. Machine learning algorithms may be utilized to detect landmarks, skin, background, and distractors. In some embodiments, the patient may have markers placed on the body to indicate the location of particular landmarks in the images such that the alignment between images is simplified.

Figure 4:
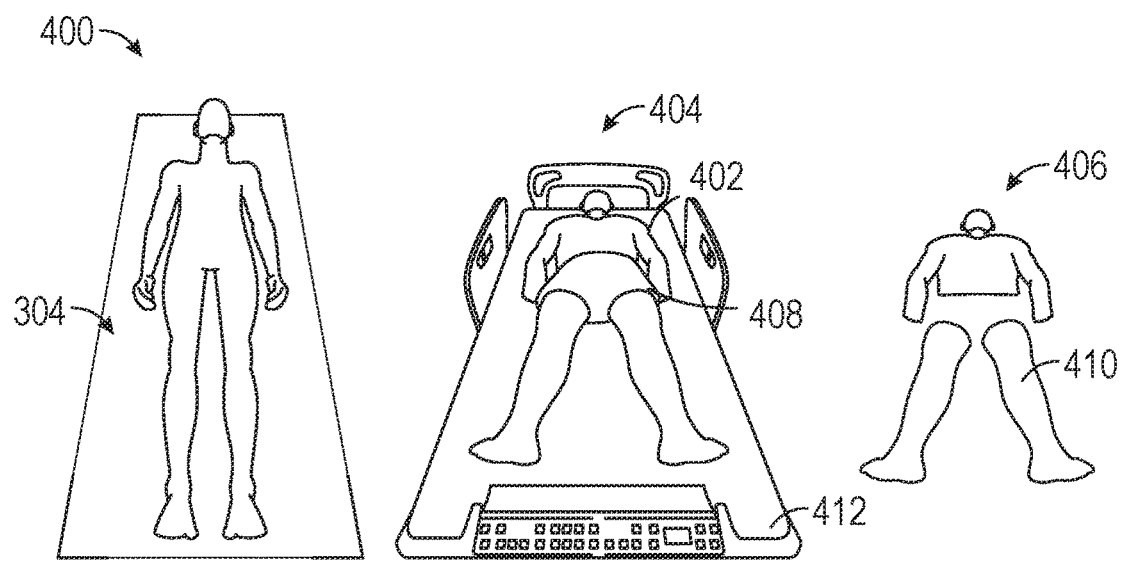
FIG. 4 depicts distractor and background removal from an image of a patient.

FIG. 4 depicts an exemplary diagram 400 presenting a process of reducing the image to displaying the skin 410 of a patient 402. The first image is the first pose 304 of the pose templates 300. The second image 404 presents the patient 402 with background 412 such as a medical bed, walls, and floors. A processed image 406 depicts the patient with the background 412 and distractors 408 (e.g., a garment or covering for the patient) removed from the image.

In some embodiments, the first pose 304 is presented to the user via the display screen 204. The user obtains the image of the patient 402 by aligning the patient 402 in a live view with the first pose 304 overlaid in the display screen 204. Subsequent image analysis removes the background 412 such as the bed and any other non-patient background. In some embodiments, a Neural Network analyzes the image or combination of the image and depth information to identify the patient in the scene. The system may use the pose information to improve the separation of background from the patient 402. Further, a garment, sheet, bandage, or other medical device, referenced herein as the distractor 408, may cover portions of the patient 402. The system may use a Neural Network to identify and differentiate skin from the distractors 408 to avoid labeling them as wounds. The processed image 406 has the distractor 408 and the background 412 removed such that the processed image 406 may be used for further analysis of the skin 410 of the patient 402. Further, removing the background 412 and the distractor 408 reduces the data in the image, and the burn analysis and modelling can be performed only on data depicting the skin 410 of the patient. It may be assumed that there is no burn at covered areas (i.e., covered by the distractor 408) and covered skin surface area is estimated to ensure the total surface area is included in the TBSA burn score. The user may leave any burned regions exposed such that there are no covered burns when obtaining the image. Therefore, all burns may be captured by the camera system 200 for analysis and capturing of known unburned areas can be skipped.

In some embodiments, the background 412, the distractors 408, and the body and skin 410 of the patient 402 may be recognized. The skin 410 of the patient 402 may be separated from the background 412 in the image using at least one machine learning algorithm such as, for example, neural networks, decision trees, statistical algorithms, and any other algorithm that may assign values to detected differences in the images. For example, at least one Convolution Neural Network (CNN) may be used to recognize the location of the patient's skin 410, the background 412, and the distractors 408. In general, the application, utilizing a trained CNN, may analyze pixels in the image to determine the edges of the patient 402 in the image of the patient. As described above, because the patient was posed, and the pose presented on the display screen 204 is overlaid such that the patient 402 generally aligns with the displayed pose, all images taken with the same pose template will be similar to each other. Therefore, training a machine learning algorithm to accurately identify the edges of the body of the patient 402 requires less training examples and is less sensitive to variation in skin tone and scene lighting. This process may also be used to avoid labeling skin of non-patient caregivers in the image.

In general, each pose template of the pose templates 300 reduces the area of the image in which specific body landmarks are expected. For each combination of pose template and body landmark, a weighing factor for each pixel may be created indicating where the landmark is more or less expected. In some embodiments, a CNN is used to recognize body landmarks in an image and may incorrectly identify multiple points as a potential location for the body landmarks. The weighting factor may be used to establish the most likely correct landmark. This process may also be used to avoid incorrectly identifying body landmarks on non-patient caregivers in the image.

In some embodiments, a CNN is trained to classify portions of an image as background 412, patient skin 410, and distractors 408. The distractors 408 may be any garment, cloth, watch, medical devices, tattoos, and any other objects that may cover the skin 410 of the patient. Similarly, the background 412 may be any object that is not part of the skin 410 of the patient 400 such as the bed and any other object that may be present in the image. The background 412 and the distractors 408 may be recognized and removed from the image for further classification of burns. The area of the patient skin 410 and distractors 412 that are covering skin is used in calculating the TBSA.

In some embodiments, the overall color and tone of the patient's skin 410 may be used to determine relative discolorations that may occur with burns. By separating out the background 412 and the distractors 408, the range of skin tones present can be more accurately assessed. Additionally, if Multi-Spectral Images are taken, masking for the areas identified as skin allows differences in reflection across the infrared spectrum to be evaluated given that the surface is skin. These techniques reduce false positive classifications and enable patient-specific color calibration which improves the accuracy of burn detection and classification.

Figure 5A:
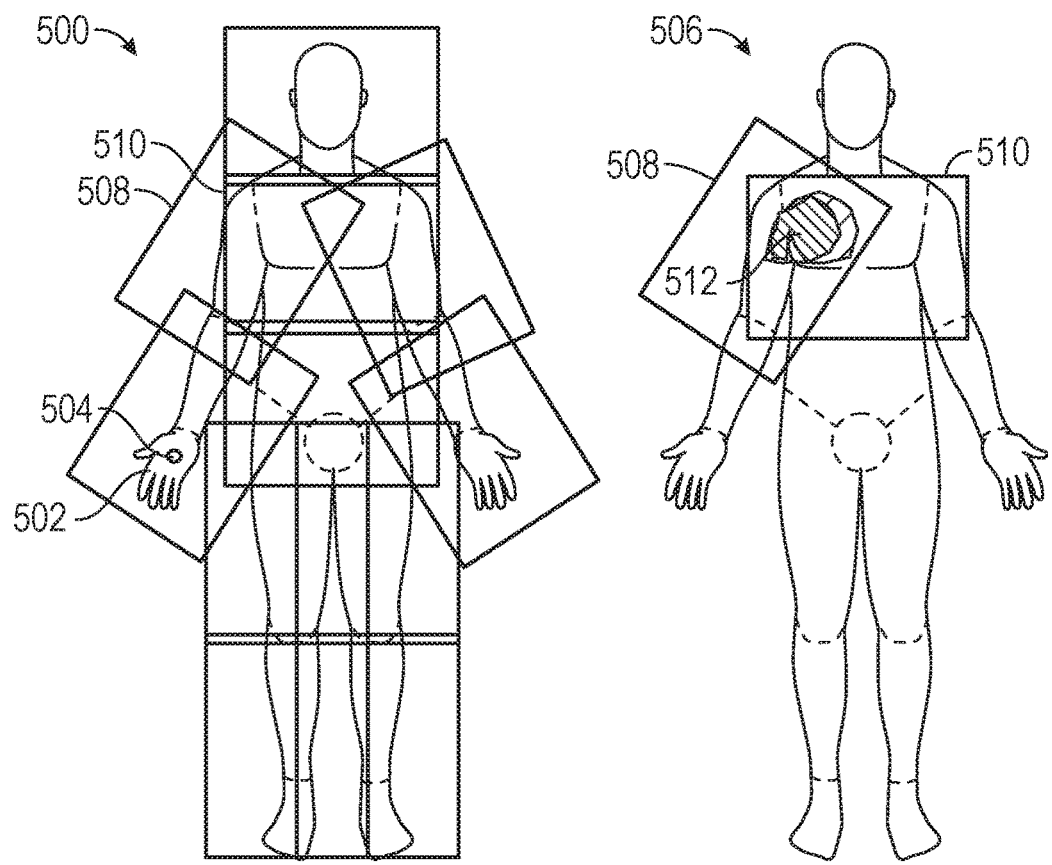
FIG. 5A depicts an embodiment of the composition of multiple patient images into an enhanced LB and recognition and localization of a burn wound.

FIG. 5A depicts an exemplary aggregated image 500 composed of a plurality of individual images of the patient 402. The plurality of individual images comprises anterior right-side shoulder template 508 and anterior torso template 510 of the body of the patient 402 that include a wound at anterior torso template 510. The pose templates 300 used here are based on anatomical body joints. Further, the plurality of individual images may be combined, morphed, and/or translated to create the accurate eLB diagram. Further still, percentage combination of body landmarks identified and image similarity in the overlapping portions of each image may be used to register these images together into the final enhanced LB diagram.

In some embodiments, body landmarks are identified and used to ensure that the pose is correct. For example, the system may determine that the right hand should be raised in order to be in the expected location for the pose template. This may be used to improve consistency of image capture and to ensure that the images taken are appropriate for analysis and aggregation.

In some embodiments, a landmark CNN is trained to detect the landmarks of the body of the patient 402. For example, the landmark CNN may detect the patient's hand 502. In other embodiments, a visible indicia 504 may be placed on the patient 402 to simplify detection of landmarks and improve registration between images. For example, identifying the location of the anterior right-side armpit in both the anterior right-side shoulder template 508 and the anterior torso template 510 allows the images to be coarsely registered quickly before using fine registration using color and label information. Accurate registration between images allows for more accurate representation of the wound at the anterior torso area in the enhanced LB because of perspective, shadow, and distraction differences in the images.

In some embodiments, the pose templates 300 and body landmarks with or without indicia 504 may be annotated with identification terms such as body part name (e.g., arm, leg, torso, head), side of body (e.g., left or right side), and anterior or posterior side. The annotated information may be used when describing the burn location relative to a known body part for example, a burn on or near the anterior torso area. This information may be used for generating patient notes in narrative format.

The reduced image 506 depicts the images using the anterior right-side shoulder template 508 and the anterior torso template 510. The anterior right-side shoulder template 508 and the anterior torso template 510 capture an overlapping region of the body in which body landmarks and/or sufficient skin area is captured so the registration algorithm does not need to compare all potential overlaps and can accurately and quickly aggregate these images together.

Figure 5B:
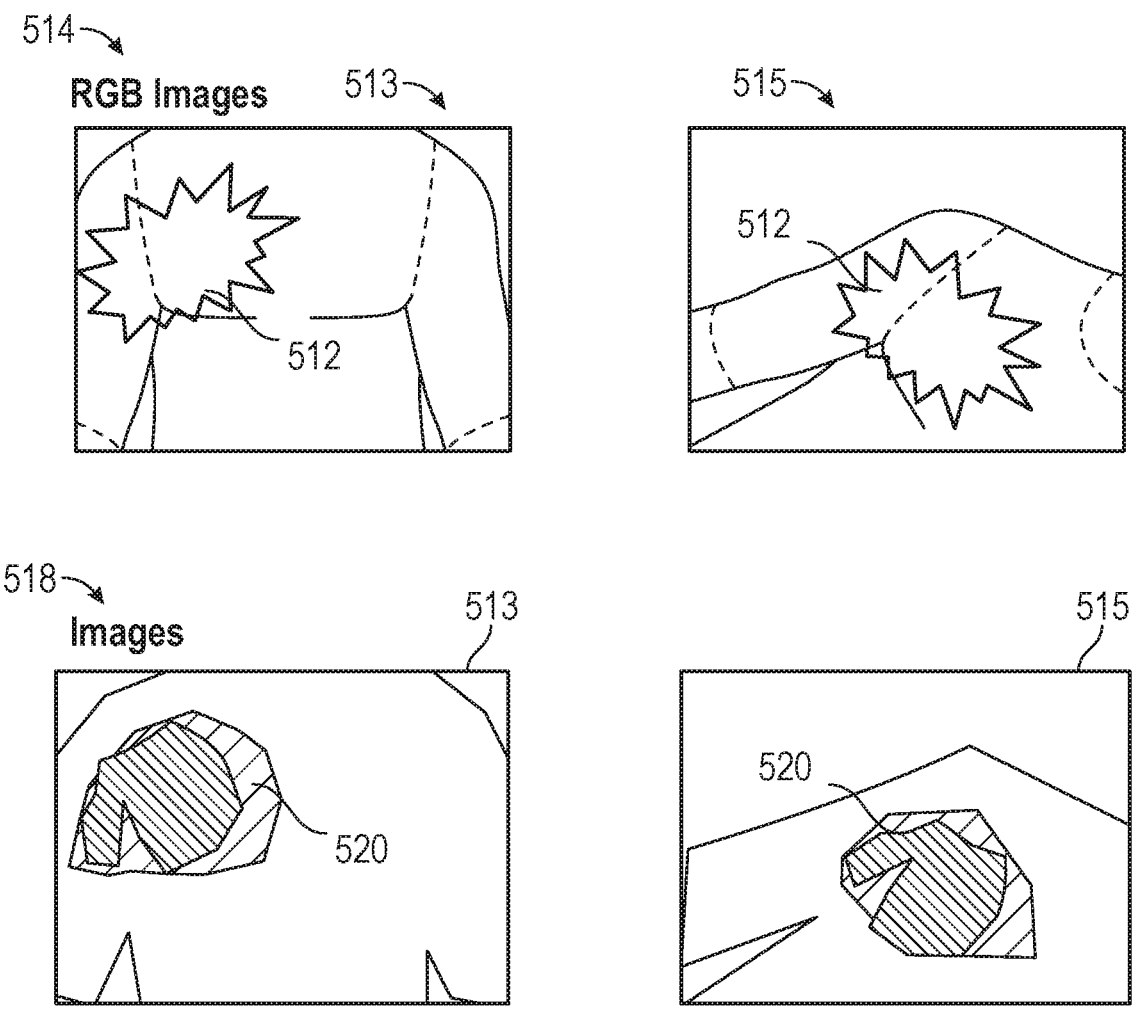
FIG. 5B depicts recognition and segmentation of background, unburnt skin, and multiple burn depths in individual images composed together.

FIG. 5B depicts a close up of the RBG images 514 of the anterior torso region and the shoulder region of the body. The burn 512 is present on the body in the close up of the RBG images 514. The images 518 are also depicted presenting the anterior torso area and the upper shoulder area. A burn model 520 is presented showing the location, surface area coverage, and the burn depth. The location of the burn 512 within each image may be determined from the CNN as described above. Because the burn 512 is detected in both images 513 and 515, the results of analysis from both images can be fused to make an accurate assessment in the enhanced LB.

Generally, the burn classification CNN algorithms may be trained using data collected using the above cameras of human and human-like animal skin. The burns in the stored training data may be annotated by burn experts such that the results of the algorithms may be compared with expert annotations to determine error. In some embodiments, combinations of machine learning, statistical algorithms, deep learning, artificial intelligence, and any other algorithms may be used to determine a best, or optimal, combination of algorithms for each analysis discussed herein. Though CNNs are discussed in embodiments herein, it should be recognized that any algorithm, or combination of algorithms, may be used for the image analysis. For example, when a CNN is referenced, any machine learning, deep learning, and statistical algorithms may be used.

In some embodiments, the skin area 410 of each image is analyzed using a CNN trained to differentiate burned from unburned skin using RGB image data. The color, tone, and texture of the skin 410 may change where the skin 410 is burned. The burn CNN may be trained from stored burn images where the burned portions of the skin 410 are labeled by an expert. Labeling allows multiple burn classes to be represented in the same image. Alternatively, historic photographs of patients can be organized by general burn severity class and the burn CNN can be trained to determine which portions of the subject image most closely match each class.

In some embodiments, the burn CNN may be trained to estimate the severity of the burn 512 using any combination of RBG images, Multi-Spectral Infrared, and thermal Images. Skin burned to different depths may exhibit variations in characteristics such as coloration, blood flow, oxygenation, hydration, inflammation, relative temperature, and exposed dermal and subdermal layers. Machine learning algorithms can identify unique signatures for these variations that indicate specific burn severity levels. In some embodiments, the burn CNN may have been trained with images of burns with known burn information on human skin or skin of animals similar to human skin such as, for example, pig skin.

In some embodiments, the severity of the burn 512 may be classified based on clinically relevant categories, for example, superficial, partial thickness, and full thickness. The classification may indicate to the medical professional the treatment regimen and procedure for handling the patient 402 and the burn 512. When the burn 512 is classified as superficial, a cream, ointment, or topical treatment may be used to treat the wound. When the burn 512 is classified as full thickness, a skin graft may be necessary. Further, an amount of water in the human body may be lost when a body is burned. The percent TBSA burned and the severity of those burns may provide an indication to the initial triage and advanced treatment regimen that is required for the patient 402. The triage and treatment regimen may be automatically provided to the medical staff treating the patient in the field based on the determined severity as described in greater detail below.

Figure 6:
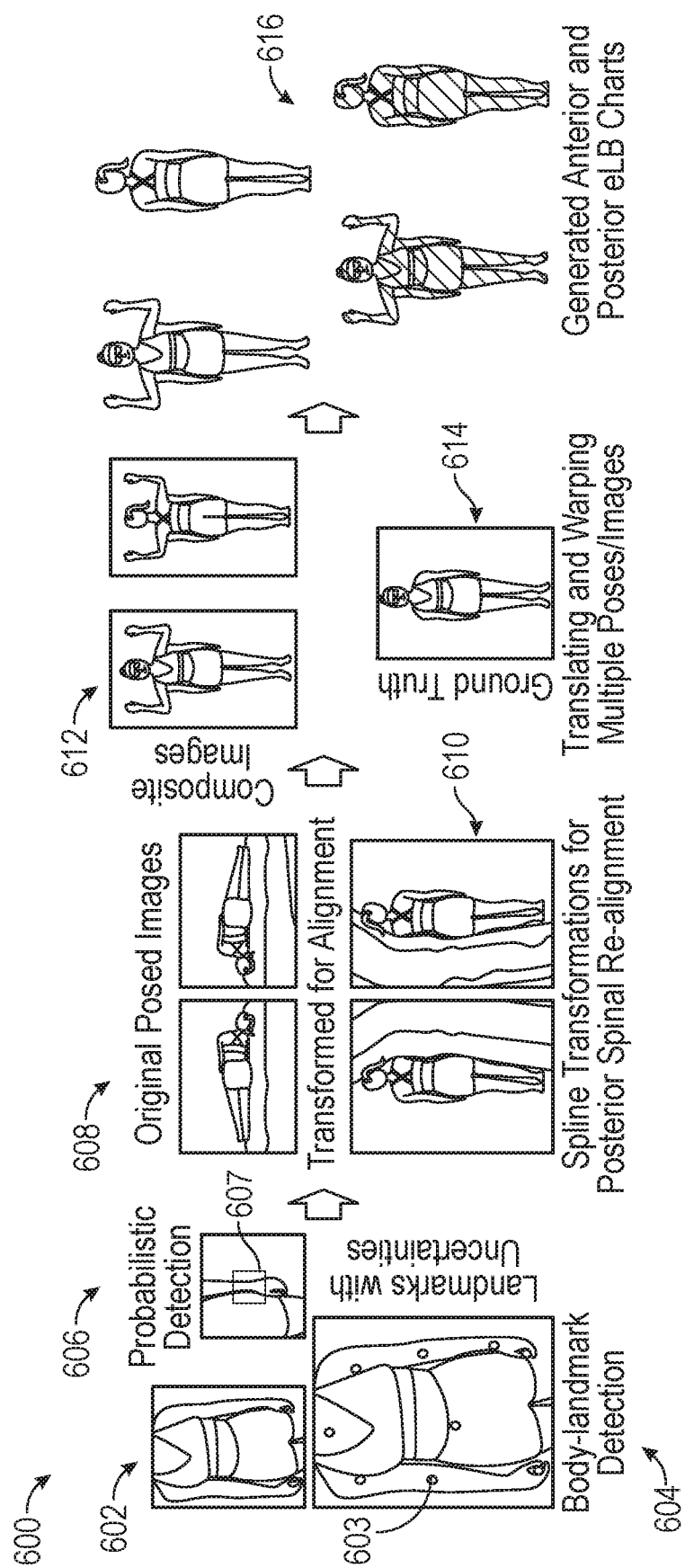
FIG. 6 depicts an exemplary flow diagram of landmark detection and augmentation of the images for generating an enhanced Lund and Brower chart.

FIG. 6 depicts an exemplary diagram presenting an exemplary process 600 of generating a two-dimensional (2D) eLB diagram and determining a TBSA percentage for a burn patient. At step 602, the plurality of images of the patient 402 are obtained using the camera system 200 as described above. The patient 402 may be posed to match a pose of the pose templates 300. The pose templates 300 may comprise a plurality of poses presented to the user on the display screen 206 of the mobile device 204. The pose template may be overlaid on the live image presented on the display screen such that the user may see both and align the patient with the pose template.

At step 604, landmark analysis may be performed to determine the different parts of the body of the patient 402. In the image presented at step 604, a set of body landmarks 603 are automatically identified in the image with uncertainties. Uncertainties exist because the detail of body landmarks vary considerably by subject resulting in a cluster of potential location candidates being produced for each body landmark. Additionally, features that look similar to body landmarks may exist elsewhere on the patient, in the background, or on a supporting clinician's body accidentally captured in the image. The potential location candidates are refined because accurate location of the body landmarks is required because they are used to both determine image transformations and aggregating images into the eLB diagram.

At step 606, the initial uncertain body landmark candidates are refined probabilistically by fusing the confidence in candidate locations with the weighted regions 607 that indicate where a given landmark is expected in the pose template 312. Candidate locations for each body landmark are scored and ranked, with the best score representing the most likely location for the body landmark. This process eliminates candidates significantly out of place and produces a single location that best represents each body landmark position within the image. Registering a plurality of images together such at body landmarks in common are co-located in the resulting aggregated image results in a set of affine transformations that minimize the effects of an imperfect patient pose with respect to the pose template 300. It should be understood that the algorithm presented here is exemplary and any method of determining an error in the image to template comparison and a likelihood of correctness may be used.

Step 608 depicts non-affine image transformations applied to the original image to morph the original image to a standard orientation that is better aligned with the final eLB pose. When the images are obtained with the camera system 200 the patient 402 is frequently posed imperfectly with respect to the idealized pose templates 300 on the display screen 206. Typically, burn patients are in pain such that taking additional time to perfect the pose or the use of poses that put undesirable pressure on the burned areas. Specifically, supports such as mattresses and pillows are flexible and change with patient weight distributions resulting in a curvature of the body in prone poses depicted at step 608. As depicted at step 608 the unmorphed image of the patient shows the patient with their head reclined and the patient's spine is not straight as is desired in the eLB. By establishing a spline through the body landmarks such as head, neck, and spine, and inferring points between body landmarks along the legs in the image, and morphing the image to straighten that spline, the image is morphed correct the body curvature. The morphed image at step 610 depicts the bed morphed and the patient's spine aligned vertically along the centerline of the body. Both the left and right side posterior poses are morphed so they can be merged to create a single posterior eLB diagram without requiring the patient to stand or lie on their front, which is often impractical for burn patients.

At step 612 the background for each image is removed and a composite image is created. The plurality of images obtained by the camera system 200 may be combined into a composite 2D image for the anterior and posterior views as depicted in steps 612 and 614. The composite image may be used to combine the burn coverage from multiple images such that the surface area is counted but not counted more than once. When the composite image is created, a full 100% body coverage (or a vast majority of body coverage, e.g., 80%-100%) may be used to determine and present the TBSA percentage based on the actual patient shape and size, and represent burns on an eLB diagram that more closely represents the specific patient.

The composite image produced at step 612 above, approximates an actual full-body single image of the patient 402 in the eLB pose. However, using a full-body pose template as depicted in the ninth pose 318 is often not feasible in burn cases unless the patient 402 can stand on their own and the user can achieve the necessary distance to fit them entirely in the camera's image frame. Additionally, separate closer poses may provide higher resolution and more direct views of the burn surface for classification, and enable clinicians to reference back to close up images if necessary.

At step 616 the anterior and posterior 2D eLB charts may be presented using anterior and posterior composite images. The anterior and posterior eLB charts may provide nearly 100% body coverage in a two-dimensional format. The eLB charts may be rendered to include any combination of the patient-specific body outline, the composite image, and the labels for skin, distractors, and burn classifications. In some embodiments, severity of burns may be represented by specific colors overlaid on the eLB diagram. Further still, treatment may be provided such as intravenous fluid amounts and if skin grafts are required.

Figure 7:
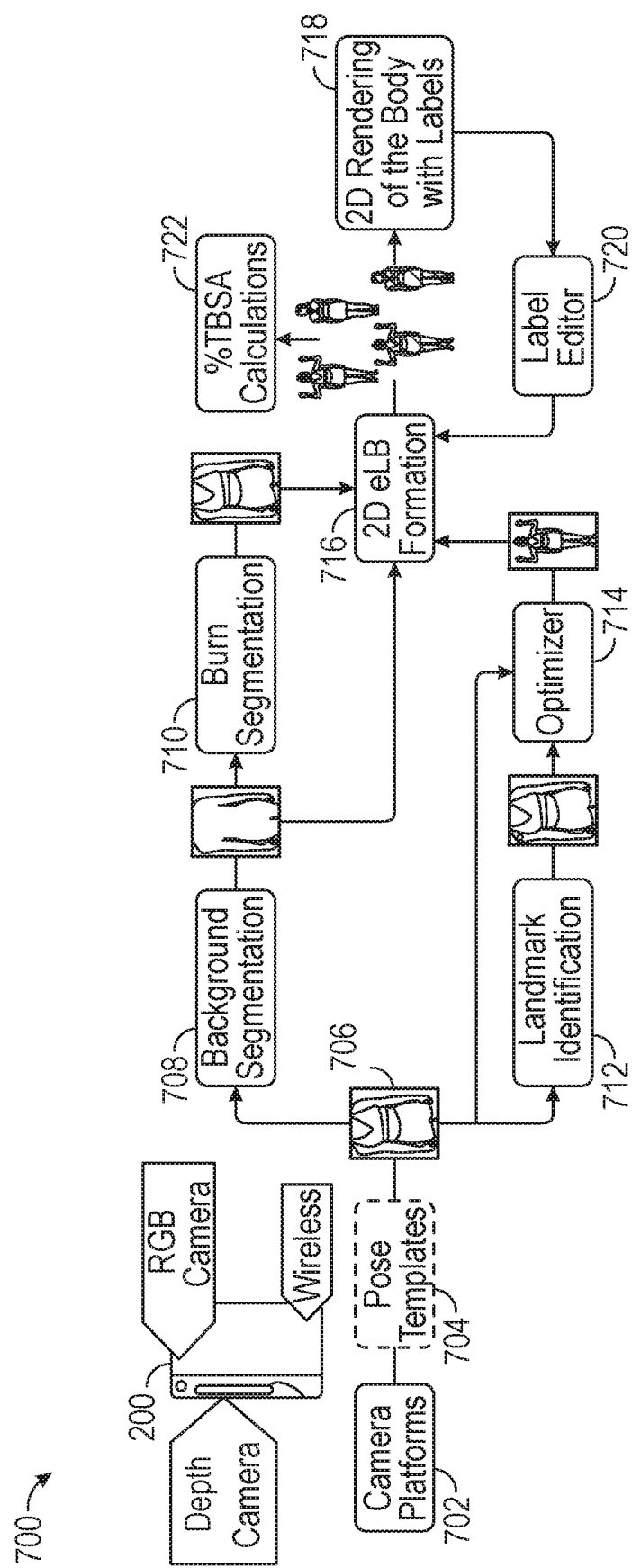
FIG. 7 depicts an exemplary flow diagram for generating a two-dimensional enhanced Lund Brower chart.

FIG. 7 depicts a flow diagram of an exemplary process 700 of determining the eLB and TBSA score in a two-dimensional model. At step 702, the camera platform 200 may be used to present the pose templates 300 at step 704 and obtain the plurality of images of the patient 402 shown at step 706. The camera system 200 may be wireless and a handheld tablet as shown in FIG. 7 such that the user may easily manipulate the camera system 200 to obtain the images in accordance with the pose templates 300.

At step 708, the background 412 is determined and removed as described in embodiments above. The background 412, distractors 408, and the skin 410 may be determined using machine learning algorithms. The background 412 and the distractors 408 may be removed from the image such that the skin 410 can be analyzed for burn area detection and classification.

At step 710, the camera system 200 uses machine learning algorithms to analyze the skin 410 and determine of the severity and location of burns on the skin 410. Relative skin discoloration and texture, or multi-spectral signatures for burn characteristics may be used to train the algorithms to detect the location and severity of the burns shown in each image.

At step 712, the system may identify landmark locations in each of the images as described in embodiments, above. The images may be analyzed to determine position of key body parts such as hands, elbows, shoulders, neck, chest, groin, knees, feet, and other body parts as appropriate for the pose template 300 that the image of the body of the patient 402 may be standardized and images can be registered together accurately and efficiently.

At step 714, The image registration may be optimized and images may be morphed and transformed as described in embodiments above. The images may be morphed and aligned such that the patient's body in the image of the patient's body closely aligns with the pose template 300 and the desired eLB pose. In some embodiments, the plurality of images may be combined to generate a composite image as described above. The composite image may allow for presentation of the anterior and posterior two-dimensional eLB charts and determination of the full TBSA percent.

At step 716, the composite images and the burn classification results are combined using the same morph and transformations as the image above to form the eLB. The eLB may comprise the composite images with a burn colored identification overlay on the two-dimensional anterior and posterior eLB images.

At step 718, the two-dimensional posterior and anterior images may be generated with labels. The labels may indicate any patient information such as name, date of birth, social security number, height, hair color, tattoos, birth marks, and any other distinguishing features and personal information. Further, the labels may indicate anatomy, burn location, burn depth, and any other burn and wound information. Further still, the labels may indicate skin areas not directly viewable because of distractors 408 or poses not captured. In some embodiments, selecting a point on eLB may direct the system to present the images that contributed data to that point of the eLB image and their associated burn detection data which can be edited.

At step 720, the eLB with labels may be presented to medical professionals for assessment and amendment. The medical professionals may review and edit the images and the labels for accuracy. The medical professionals may be in the field with the patient 402 such that the medical professional can review the eLB and labels and compare with the body of the patient 402 in real time. In some embodiments, the medical professional may be at a remote location, such as at a hospital, and may review and edit the images and labels remotely.

At step 722, the percent TBSA burned may be determined and presented to the medical staff in the field and the medical professional online. The TBSA percent may be presented as a label on the eLB chart and may be presented with recommended treatment for the patient 402. In some embodiments, the TBSA is calculated and presented with a full body, anterior, and posterior breakdown. Further the percent TBSA burned can be computed with or without estimated surface area due to distractors or limited images, and accounting for confidence in the burn classification to provide a confidence range.

Figure 8:
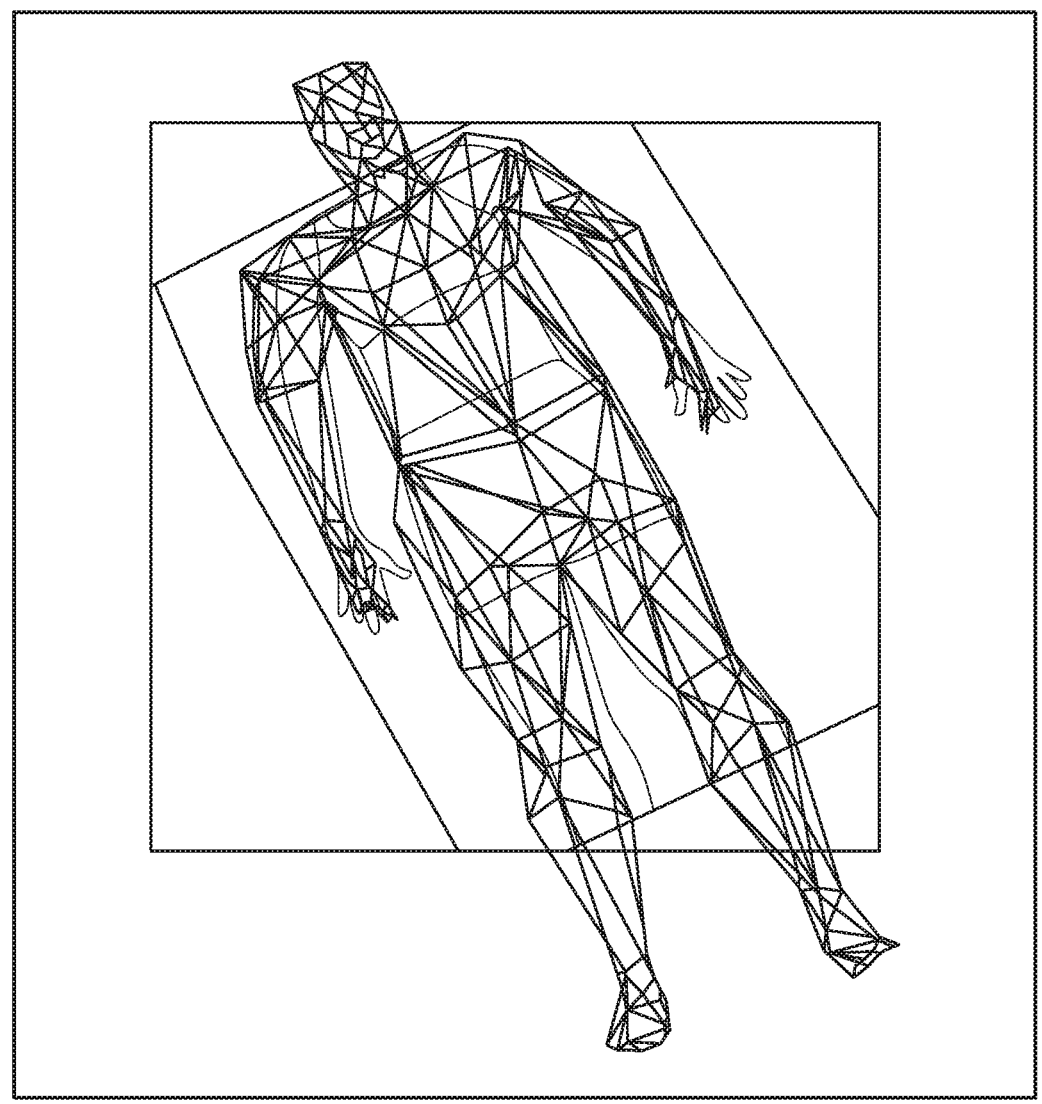
FIG. 8 depicts an exemplary mapping of an image to the texture map coordinates of a standard body mesh and resizing the mesh based on body landmarks.

In some embodiments, a three-dimensional body model is created for presentation of the eLB chart in 3D. FIG. 8 depicts an exemplary mapping of an image into the texture map coordinates used by a standard 3D mesh model of a human body. This mapping may use body landmarks and a CNN that identifies the image space locations that best correspond to coordinates in the texture map used by the 3D mesh. The standard body mesh 800 may be morphed using any combination of the depth information, such as model fitting to the point cloud, and relative proportions extracted from images. The standard body mesh 800 may be deformed to conform to the point cloud model of the patient creating a three-dimensional model of the patient 402. The mapping between image locations and texture coordinates may then be used to wrap the mesh body with the skin 410 images and data indicative of the burn 512 creating a three-dimensional model unique to the shape and characteristics of the patient 402. All labeling may be added to the body model as described above including the TBSA percent. Additionally, 3D interaction and animations, including reposing of the 3D eLB may be performed.

In some embodiments, the enhanced 3D Lund and Browder chart may be labeled with at least one of patient information, treatment regimen, a burn classification, and the total body surface area burn score. Further, the three-dimensional enhanced Lund and Browder chart may be presented as a 3D model configured to be rotated and reposed.

Figure 9:
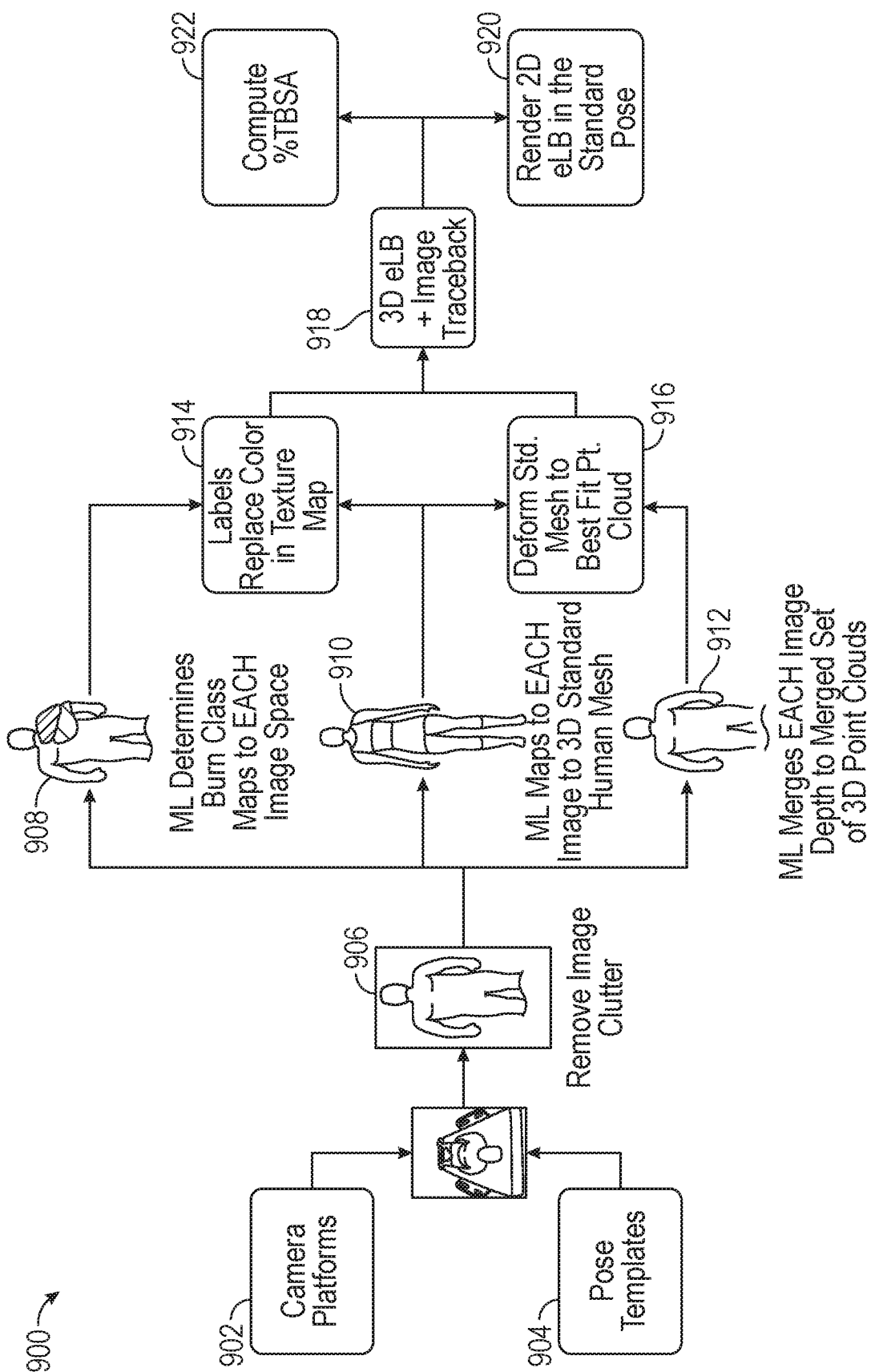
FIG. 9 depicts an exemplary flow diagram for generating a three-dimensional enhanced Lund and Browder chart.

FIG. 9 depicts an exemplary process 900 of generating a three-dimensional model of the patient 402. At steps 902, 904, and 906, the camera system 200 is operated to display the image templates 300 and obtain the images of the patient 402 as described in embodiments above. Further, one or more non-transitory computer-readable media storing computer-executable instructions is executable by at least one processor to detect the skin 410, the distractors 408, the background 412, the burns 512, and any other information necessary to generate the two- and three-dimensional models described herein.

At step 908, the machine learning algorithm determines characteristics of the burn 512 and maps the burn location and the severity to the location on the body model as described above. The data indicative of the burn 512 may be mapped to each image. Further, the burn 512 may be classified based on the CNN analysis of the severity of the burn.

At step 910, the machine learning algorithm maps each image to the three-dimensional body mesh 800 as described above. Mapping each image may produce a mapping of the skin 410 in the images to the appropriate 3D mesh surfaces. In some embodiments images and burn label data can be composited into texture maps that may be used to wrap the 3D mesh.

At step 912, data from the depth camera (with clutter and background removed at step 906) may be converted into a point cloud model that represent the size and shape of the patient 402. Body landmarks and or pose template expectations may be used for course registration. Further, a point cloud registration algorithm may be used for fine alignment optimization.

At step 914, the burn classification data for each pixel in the original image may be mapped to a texture map for the 3D model as a color value representing the burn severity or any other classes. Step 914 produces patient-specific textures for skin and burn data.

At step 916, an optimizing model fit algorithm may morph the standard 3D human shaped mesh to best fit the point cloud and any relative image sizes using the pose template or body landmarks for initial course registration. Step 916 results in a patient-specific 3D mesh model that estimates the anatomic morphology of the patient's body 402 and thus a more accurate estimate of the total surface area and the relative area of burns.

At step 918, the three-dimensional eLB is generated by rendering patient-specific 3D mesh, wrapped with the patient-specific texture maps. The final eLB may be the unique three-dimensional model of the patient 402 including the burn 512 and labels with the background 410 removed and optionally the distractors 408 removed. The eLB may be reviewed by medical staff for accuracy and correctness, and edited in the same manner as the 2D eLB describe above.

At step 920, the two-dimensional eLB may be generated from the three-dimensional eLB or from the method described in FIGS. 6-7. In some embodiments, the two-dimensional eLB may be displayed in a standard pose, a combined pose described above, or any pose desired by the user to best view the burn 512. Because the two-dimensional eLB is generated from the three-dimensional eLB, the presented pose of the two-dimensional eLB may be customizable to simulate potential treatment plans and physical supports.

At step 922, the TBSA score may be computed. The TBSA score may be computed from the 3D model which may be more accurate than a 2D version because it includes surface rounding that may not be completely reflected in 2D anterior and posterior profiles. Further, the TBSA score may be presented to the medical staff for review. Further still, treatment plans and advice may be presented on the eLB chart along with the TBSA score.

In some embodiments, the automatic alerts may be sent to medical staff that provide treatment and triage procedures. In some cases, there may be a plurality of patients. A plurality of camera systems may be communicatively connected such that a plurality of patient analysis is performed concurrently. To organize the medical staff, a triage procedure may be generated with the eLB chart. The triage procedure may comprise patient care order and treatment order. For example, three patients are admitted simultaneous. The three patients are evaluated using the camera system 200. Patient one is evaluated as superficial while patient two and patient three are evaluated as full thickness. Patient two may receive a TBSA score of 35% and patient three may receive a TBSA score of 28%. The order for care may be listed as, patient two, patient three, and then patient one. The treatment may also be provided as described above.

In some embodiments, the two and three-dimensional eLB may be presented to a medical professional at a remote facility. The medical professional may view the three-dimensional eLB via a headset presenting a three-dimensional Virtual Reality (VR) environment. In the VR environment, the medical professional may view and pose a lifelike three-dimensional representation of the body of the patient 402 with digitally added skin 410 and burn 512. The medical professional may view and pose the body and provide feedback and treatment recommendations immediately and remotely, thus saving valuable time in treating the patient 402.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

The invention claimed is:

1. A method of creating an enhanced Lund and Browder chart and determining a total body surface area burn score for a patient with burns, the method comprising:
   displaying a plurality of pose templates on a display to assist in obtaining a plurality of images;
   obtaining the plurality of images of the patient by at least one camera aligning each pose of the patient with each pose template of the plurality of pose templates on the display;
   automatically recognizing:
     patient body landmarks in the plurality of images;
     patient skin regions in the plurality of images;
     a background in the plurality of images;
     distractors in the plurality of images and classifying the distractors;
     burn locations on the patient in the plurality of images;
   combining the plurality of images to create the enhanced Lund and Browder chart; and
   determining the total body surface area burn score based at least in part on the enhanced Lund and Browder chart.

2. The method of claim 1,
   wherein the enhanced Lund and Browder chart is a two-dimensional model of the patient including burns,
   wherein the enhanced Lund and Browder chart is two-dimensional and customized to a size and a shape of the patient,
   wherein the enhanced Lund and Browder chart is a combined image from the plurality of images, and
   wherein the total body surface area burn score is a percentage of a total body surface area burned determined from the two-dimensional model.

3. The method of claim 2, further comprising:
   labeling the enhanced Lund and Browder chart with at least one of patient information, treatment regimen, a burn classification, and the total body surface area burn score; and
   presenting the enhanced Lund and Browder chart as an anterior two-dimensional pose and a posterior two-dimensional pose including the labels.

4. The method of claim 1,
   wherein the enhanced Lund and Browder chart is a three-dimensional model of the patient including the burns,
   wherein the enhanced Lund and Browder chart is a three-dimensional mesh or point cloud representing a specific patient's size and shape in three-dimensions,
   wherein a surface of the enhanced Lund and Browder chart is a combined image from the plurality of images, and
   wherein the total body surface area burn score is a percentage of the total body surface area burned determined from the enhanced Lund and Browder chart.

5. The method of claim 4, further comprising:
   labeling the enhanced three-dimensional Lund and Browder chart with at least one of patient information, treatment regimen, a burn classification, and the total body surface area burn score;
   presenting the three-dimensional enhanced Lund and Browder chart as the three-dimensional model configured to be rotated and reposed; and
   wherein the labels are presented with the enhanced Lund and Browder chart.

6. The method of claim 1,
wherein the patient body landmarks, the background, the patient skin, the distractors, and the burn locations are recognized by at least one convolution neural network,
wherein the at least one convolution neural network is processed on a mobile device, and
wherein the mobile device is communicatively coupled to the at least one camera.

7. The method of claim 1, wherein the plurality of images are transformed or morphed based in part on body landmarks before being composed into the enhanced Lund and Browder chart.

8. The method of claim 1, wherein the at least one camera is configured to generate at least one multi-spectral image in an infrared range; and
further comprising determining burn severity from the plurality of images using the at least one multi-spectral image in the infrared range.

9. The method of claim 1,
wherein the at least one camera senses depth; and
further comprising generating a three-dimensional model of the patient's body,
wherein the three-dimensional model of the patient's body is generated by fitting a three-dimensional mesh to a point cloud of the patient's body.

10. The method of claim 1, wherein the plurality of images and the burn locations are mapped to a three-dimensional model of the patient's body.

11. A system for creating an enhanced Lund and Browder chart and determining a total body surface area burn score of a patient with burns comprising:
at least one camera configured to obtain a plurality of images of the patient;
a mobile device comprising at least one processor and a display,
wherein the at least one camera is communicatively coupled to the mobile device; and
one or more non-transitory computer-readable media storing computer-executable instructions that, when executed by the at least one processor, perform a method of creating the enhanced Lund and Browder chart and determining the total body surface area burn score, the method comprising:
displaying a plurality of pose templates on the display of the mobile device to assist in obtaining patient poses in the plurality of images;
obtaining the plurality of images by the at least one camera aligning each pose of the patient with each pose template of the plurality of pose templates on the display;
automatically recognizing:
patient skin regions in the plurality of images;
a background in the plurality of images;
distractors in the plurality of images and classifying the distractors;
burn locations on the patient in the plurality of images;
combining the plurality of images to create the enhanced Lund and Browder chart; and
determining the total body surface area burn score based at least in part on the enhanced Lund and Browder chart.

12. The system of claim 11, wherein the at least one camera is configured to obtain at least one of a multispectral infrared image.

13. The system of claim 11, wherein the at least one camera is configured to obtain at least one RGB image from a visible light spectrum.

14. The system of claim 11, wherein the at least one camera is configured to obtain at least one depth image representing a distance from the at least one camera to the patient.

15. The system of claim 11, wherein a computer display is mounted to the at least one camera.

16. The system of claim 11, wherein the method further comprises presenting the enhanced Lund and Browder chart as an anterior two-dimensional pose and a posterior two-dimensional pose with at least one label, wherein the at least one label is at least one of the total body surface area burn score and a classification of the burns.

17. The system of claim 11, wherein the method further comprises presenting a three-dimensional enhanced Lund and Browder chart configured to be rotated and reposed with at least one label, wherein the at least one label is at least one of the total body surface area burn score and a classification of the burns.

18. The system of claim 11, wherein the method further comprises:
presenting, on the display with the enhanced Lund and Browder chart, an option for a user to access an image of the plurality of images that make up the enhanced Lund and Browder chart,
wherein labels in the image are editable and comprise information indicative of burn location and severity;
generating, automatically, a new enhanced Lund and Browder chart; and
determining a new TBSA burn score based at least in part on updated labels.

19. One or more non-transitory computer-readable media storing computer-executable instructions that, when executed by at least one processor, perform a method of creating an enhanced Lund and Browder chart and determining a total body surface area burn score of a patient with burns, the method comprising:
displaying a plurality of pose templates on a display of a mobile device to assist in obtaining patient poses in a plurality of images;
obtaining the plurality of images by at least one camera associated with the mobile device aligning each pose of the patient with each pose template of the plurality of pose templates on the display;
automatically recognizing:
patient body landmarks in the plurality of images;
skin of the patient in the plurality of images;
burn locations on the skin of the patient in the plurality of images;
distractors in the plurality of images and classifying the distractors, combining the plurality of images to create the enhanced Lund and Browder chart;
determining the total body surface area burn score; and
presenting the enhanced Lund and Browder chart and the total body surface area burn score via the mobile device.

20. The method of claim 19, further comprising:
determining a severity of the burns from the plurality of images;
classifying the patient based at least in part on the total body surface area burn score and the severity of the burns; and
generating full body anterior and posterior images consistent with a size and a shape of the patient's body by combining the patient body landmarks, the plurality of pose templates, and image morphing to compose the plurality of images.

\* \* \* \* \*